United States Patent [19]
Storer

[11] Patent Number: 6,113,605
[45] Date of Patent: Sep. 5, 2000

[54] PROSTHESIS INSERTER

[75] Inventor: John Andrew Storer, Bayeux, France

[73] Assignee: Benoist Girard & Cie, France

[21] Appl. No.: 09/257,306

[22] Filed: Feb. 25, 1999

[30] Foreign Application Priority Data

| Mar. 2, 1998 | [GB] | United Kingdom | 9804471 |
| Nov. 26, 1998 | [GB] | United Kingdom | 9825939 |

[51] Int. Cl.⁷ .................................................. A61B 17/00
[52] U.S. Cl. ............................................. 606/99; 606/86
[58] Field of Search ......................... 623/16, 23; 606/99, 606/86

[56] References Cited

U.S. PATENT DOCUMENTS

| 5,064,427 | 11/1991 | Burkinshaw | 606/99 |
| 5,443,471 | 8/1995 | Swajger | 606/99 |
| 5,989,259 | 11/1999 | Penenberg | 606/99 |

*Primary Examiner*—David Isabella
*Attorney, Agent, or Firm*—Lerner, David, Littenberg, Krumholz & Mentlink, LLP

[57] ABSTRACT

An insertion system for a prosthesis has an inserter with a box-like attachment device mounted therein. The attachment device has an end wall, a bottom wall and a pair of sidewalls with a crossbar spaced from said bottom wall extending between said side walls. A resilient adapter engages a trunion on the prosthesis and includes an arm designed to engage the attachment device by locking under the crossbar. To prevent rotation a spring-loaded retractable rod is mounted within the inserter and can be selectively moved into and out of engagement with a locating element on the prosthesis.

25 Claims, 9 Drawing Sheets

PROSTHESIS INSERTER

BACKGROUND OF THE INVENTION

1. Field of the Invention

This invention relates to a prosthesis inserter which is particularly, although not exclusively, applicable for use for inserting a femoral stem prosthesis.

2. Description of the Prior Art

It is particularly difficult to grip the femoral component of a total hip prosthesis without damaging the stem. Damage to a femoral component in the region of the neck may lead to a reduction in the fatigue life of the component since the damage may lead to the initiation of cracks. Furthermore, damage to the spigot of a modular design, that is a stem component in which heads of different sizes or shapes can be fitted to a spigot trunion, may lead to problems with the engagement of the prosthetic femoral head on the stem. Consequently there are many designs of stem introducing instruments which employ protection of the spigot and the neck of the stem.

It has also been found with earlier designs which clamp on only the spigot of the stem that, although the inserter may be tightly clamped to the spigot, there can be rotary movement. The rotary movement can be a nuisance during insertion and can result in an incorrect and misaligned insertion. Improving the force used to clamp the spigot to prevent the rotary movement is likely to cause damage to the spigot.

In many cases it has been found necessary to include a feature on the stem, such as a dimple or a depression into which the stem introducing instrument engages to provide a secure attachment of the stem to the introducer. With such a design of stem introducing instrument, it is usual to achieve engagement onto the stem by advancing an attachment element which engages with the stem. In previous designs the method of advancement has required the surgeon to use two hands to advance the attachment element to secure the stem and, more importantly, has required two hands to be used to effect release. The use of two hands is indicative of the complexity of the methods of engagement and, for a cemented stem, the action to disengage the stem introducing the instrument may lead to a disruption of the partially cured cement mantle which may impair the long term results of the implantation. It is therefore desirable to achieve a design of prosthesis implantation inserter instrument which enables the stem to be releases with one hand with the minimum disturbance to the cement mantle.

The present invention is intended to overcome both the problems referred to above.

SUMMARY OF THE INVENTION

According to the present invention, a prosthesis implantation inserter comprises attachment device for securing and holding the prosthesis to be implanted, a locator is spaced away from the attachment device and is adapted to engage the prosthesis to prevent axial and angular movement thereof in relation to the insertion axis of the inserter and a release is adapted for single handed operation for releasing the attachment device or the locator or both.

The construction may be arranged so that the implantation loads applied to the inserter are transmitted to the prosthesis to be implanted through the attachment device, alternatively the construction can be such that implantation loads applied to the inserter are transmitted to the prosthesis to be implanted through the retractable locator. The attachment device is preferably adapted to attach to the head spigot of a femoral component to be inserted and may comprise a resilient adapter shaped to surround the spigot of the prosthesis and the provision of engagement structure which grasps the resilient adapter.

Thus, the resilient adapter may include an engagement claw or claws which locate in the engagement structure.

In another embodiment the resilient adapter can be in the form of a releasable collet having a flange which is adapted to engage beneath the head spigot of the prosthesis to be implanted and a release for retaining the collet in place. If desired the collet can be split.

With this construction operating mechanism can be included for simultaneously actuating the releasable collet and the releasable locator. The releasable locator can be adapted to engage a location feature on the prosthesis to be implanted and such a feature can be provided by a side or sides of the prothesis. With this arrangement the location means can be in the form of a retractable bifurcated portion which engages the sides of the prosthesis.

In another construction the attachment device can include an attachment element adapted to attach to the head spigot of said femoral component, and to also receive said locator. This attachment element can have means for firm attachment to the inserter.

Thus the attachment element can have tapered socket dimensioned to co-operate with the spigot of said prosthesis and a tapered socket to co-operate with a suitable portion of the inserter adjacent said locator.

In a preferred embodiment that attachment element is adapted to engage the proximal shoulder of the femoral component to be implanted.

The releasable locator can be adapted to engage a location feature on the prosthesis to be impanted and such a feature can be provided by a side or sides of the prosthesis. With this arrangement the locator can be in the form of a retractable bifurcated portion which engages the sides of the prosthesis.

Alternatively or additionally the locator may include a retractable pin adapted to engage a location opening in the prosthesis. The device may include a body portion which extends along the axis of insertion, a handle and a trigger for operating the releasable locator.

The releasable locator acts to lock the prosthesis in position to prevent rotation and the device can thus easily be removed from the prosthesis once it has been inserted by simple operation of the operating trigger which acts to remove all the connections.

In the earlier construction referred to above in which the resilient adapter includes a claw or claws the operation is again single handed because the locator can be withdrawn and the attachment device simply disconnected.

If desired can be included to hold the retractable locator in a withdrawn position thus assisting removal.

BRIEF DESCRIPTION OF THE DRAWINGS

The invention can be preformed in various ways and some embodiments will now be described by way of example and with reference to the accompanying drawings in which.

DESCRIPTION OF THE PREFERRED EMBODIMENT

As shown in FIGS. 1 to 5 a prosthesis the preferred inserter comprises a main body component 1 having a longitudinal axis and which is the insertion axis, indicated by dashed line 2. The main body component 1 carries an angled extension 3 on which is integrally mounted attachment device 4 for holding a femoral prosthesis component indicated by dashed lines 5. The main body component 1 has a cylindrical support 6 on which is carried a compression spring 7 which bears against a sliding collar 8 also mounted on the cylindrical support 6. The collar 8 is provided with a circumferential groove 9 and is connected to an operating rod 10.

Figure 1:
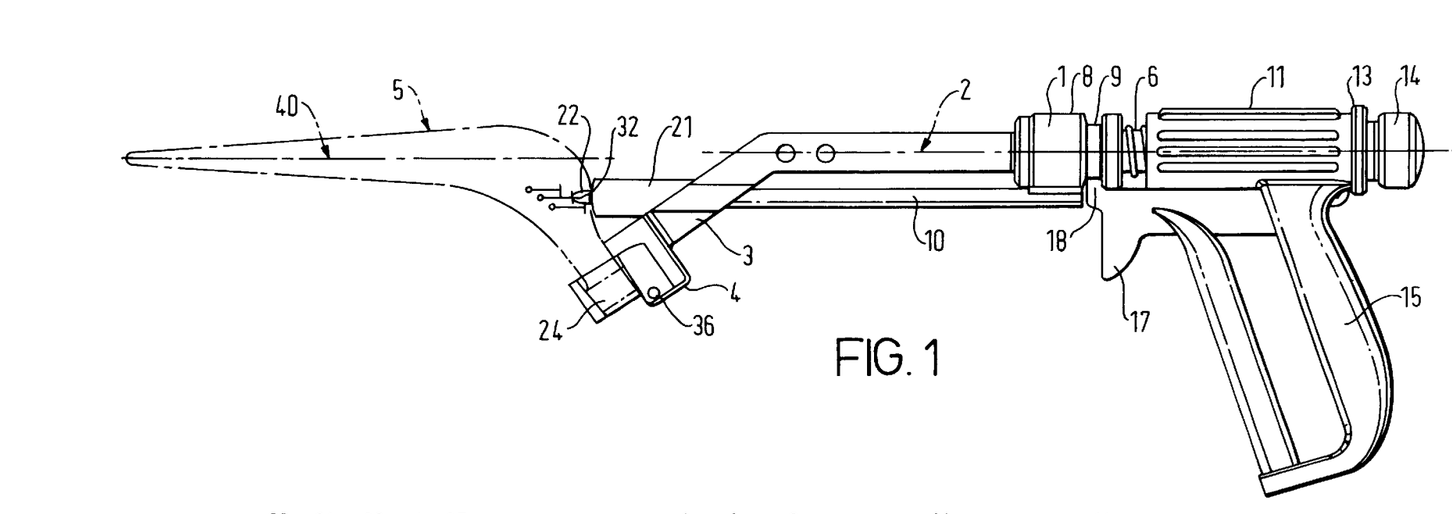
FIG. 1 is a side elevation of a first construction of prosthesis inserter according to the invention with a prosthesis to be inserted location in position.
Figures 3, 4, 5:
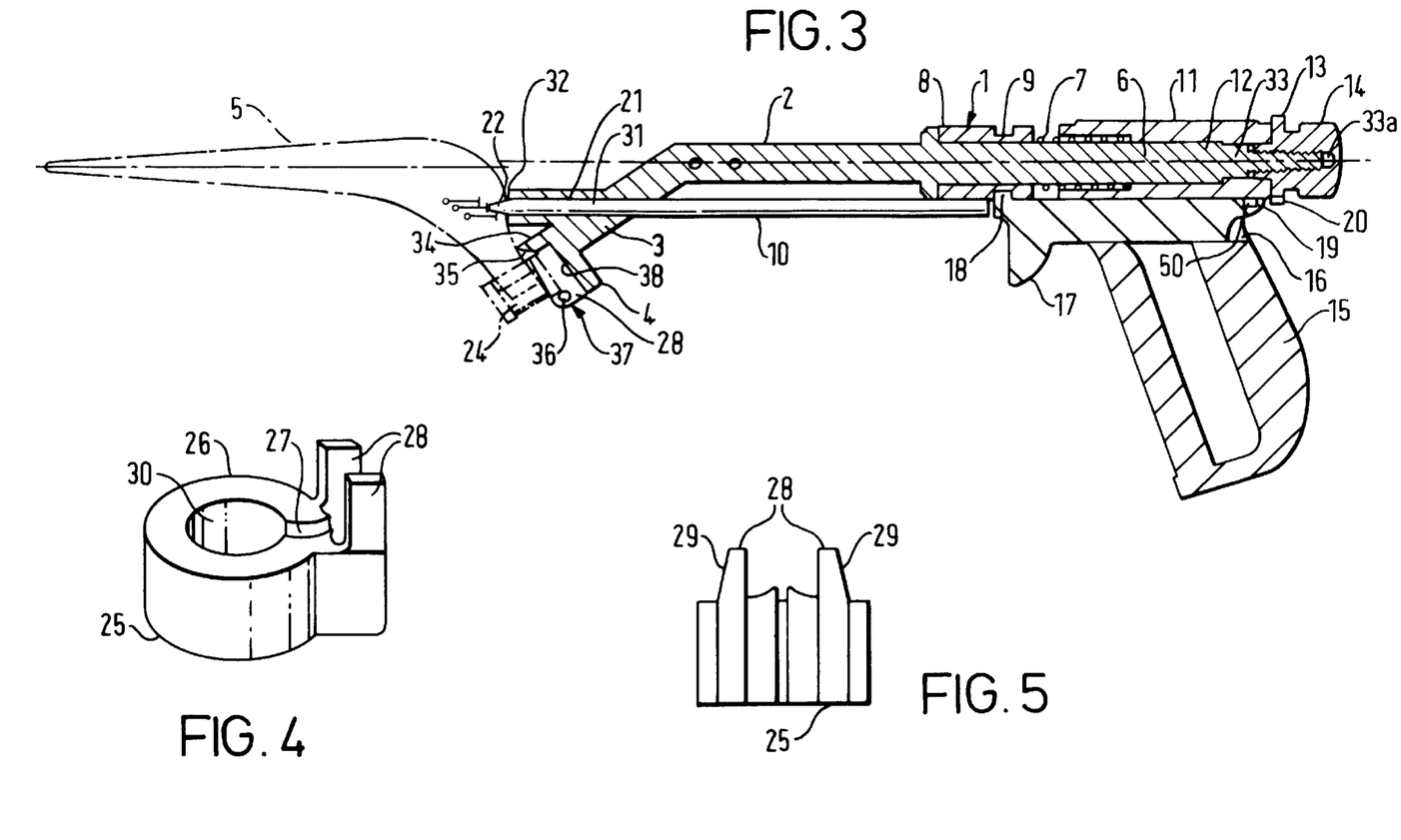
FIG. 3 is a cross-sectional side elevation of the inserter shown in FIGS. 1 and 2 on the lines III—III of FIG. 2.
FIG. 4 is an isometric view of an adapter for use with the inserter.
FIG. 5 is a end elevation of the adapter shown in FIG. 4.

In the preferred embodiment the spring 7 is housed within a casing 11 having a cylindrical bore 12 to enable it to be carried on the cylindrical support 6 and the end of this support has a square section portion 33 and a screw threaded extension 33a on which is located a rotatable locating disc 13 and a screw threaded lock knob 14. The end of the bore 12 is of square cross-section to locate on the square section 33 of the support 6.

The lower part of the casing 11 is extended to form a handle 15 and a guide slot 16 is provided between the handle and the main part of the casing to house a trigger 17. The trigger has an upstanding abutment 18 which locates in the annular groove 9 and is also provided with an extension 19 which is shaped to fit into an opening 20 provided on the outer circumference of the disc 13.

The end of the rod 10 spaced away from the handle 15 is guided in an extended bore 31 located in a projecting boss 21 on the extension 3 and the outer end 22 of the rod 10 is shaped, in this example in the form of a truncated cone, to fit closely into a location feature in the form of a location opening 23 in the prosthesis 5.

The prosthesis is of modular design, that is a stem component on which heads of different sizes or shapes can be fitted to a trunion or spigot 24.

In order to prevent damage to the spigot an adapter 25 is provided which is shown in FIGS. 4 and 5. This adapter can be made from any suitable material, for example metal or a plastics material such as a resilient polycarbonate, and is in the form of a collar 26 one side of which is split to provide an opening 27. In the preferred embodiment a pair of claws 28 extend one on each side of the opening 27 and their outer faces 29 are chamfered, as is most clearly shown in FIG. 5.

The internal bore 30 of the collar is slightly less that the outer circumference of the tapered spigot 24 so that it is a push fit onto it, the natural resilience of the material allowing the collar to be placed in position.

Figure 2:
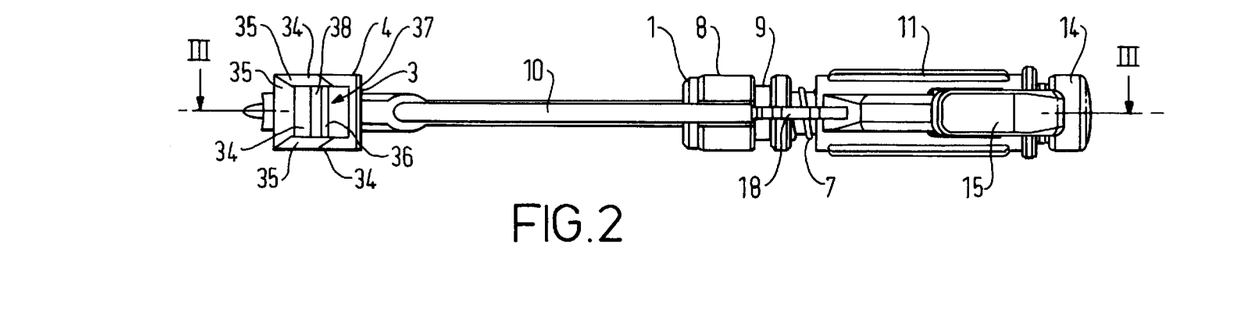
FIG. 2 is a plan view from below of the inserter shown in FIG. 1.
Figure 17:
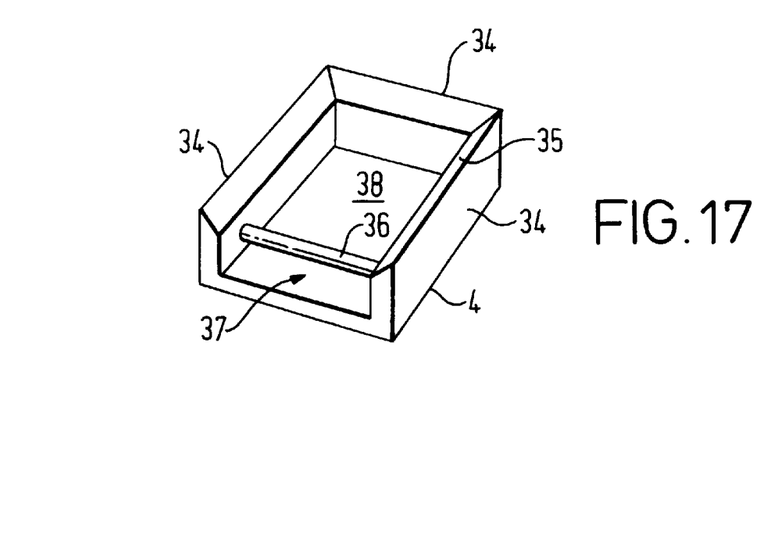
FIG. 17 is a diagrammatic perspective view of the tray which forms the attachment device in the embodiment shown in FIGS. 1 to 5.

The preferred attachment device 4 is in the form of a substantially square tray, as is mostly clearly shown in FIGS. 17 and 2. The tray has three upstanding side walls 34 the upper portions of which are chamfered at 35. The remaining side is open apart from a bar 36 which extends between the two parallel side walls 34 and leaves beneath it an opening 37 to the base or flat floor 38 of the tray. The angle of the base of the tray is appropriate for the angle of the neck to the stem of the prosthesis to be inserted.

To attach a femoral component to be inserted adapter 25 is first placed over the spigot 24. The claws 28 are then pushed into the tray and rotated about the bar 36 so that they extend into the opening 37. The dimensions of the claws and the distance from their front and bottom faces 28A to the outer circumference of collar 26 is arranged so that the collar together with the femoral component is locked between the bar 36 and the opposed end wall 34 within the portion of the wall beneath the chamfer 35. Moreover, the width between the parallel walls 34 and the distance between the chamfered faces 29 and the remainder of the walls of the claws relative to the two parallel walls 35 is arranged so that there is a constricting effect tending to close gap 27 in the collar so that the spigot of the femoral component is tightly clamped.

With the femoral component located on this attachment device it will be seen that the center line of the femoral component, indicated by reference numeral 40, and the center line 2 of the inserter are substantially in axial alignment. In the construction being described the alignment is slightly displaced but the displacement or the alignment could be as desired.

If this were the only means of holding the prosthesis onto the inserter then there is the possibility of the spigot rotating in the bore, despite the clamping effect. The prosthesis is however provided with a location feature in the form of the location opening or depression 23 in the shoulder of the prosthesis. As the prosthesis is rotated into the attachment device the trigger 18 is retracted thus compressing the spring 7 and moving the rod 10 rearwardly. Once the locking pin is approximately in position the trigger can be released and slight further movement will allow the engagement locking pin to move into place. Thus the prosthesis is now held by the attachment device 4 and the retractable locator provided by the pin 10 engage the prosthesis at a point spaced away from the attachment means and prevent axial and angular movement in relation to the insertion axis 2 of the inserter.

Because the pin 10 is biased into the location opening 23 any downward insertion load by the surgeon whilst the prosthesis is implanted will not be carried by the pin 10 but by the end 32 of the boss 21 bearing against the shoulder of the prothesis and is also partly carried by the cranked stem 3 which transfers the load to the prosthesis through the attachment device 4. The pin 10 merely acts to prevent axial and angular movement.

Once the surgeon has completed the insertion and provided the loading on the cement the inserter can be removed by one hand, merely be operating the trigger 17 to remove the rod 10 from the location opening 23 to release the locator and by then simply rotating the inserter about the pin 36 so that the attachment device are also released without unnecessarily disturbing the implanted prosthesis and without having to use both hands.

Figure 7:
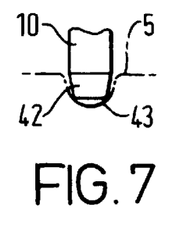
FIGS. 7, 8 and 9 show alternative forms of locator.
Figure 8:
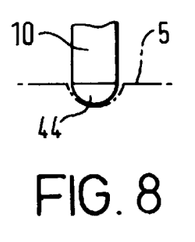
Figure 9:
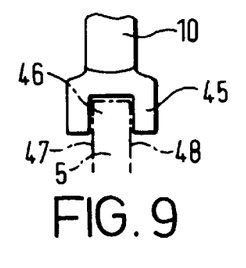

FIGS. 7, 8 and 9 show various alternative embodiments to provide the location of the inserter on stem 5 and which can be employed in any of the embodiment described herein. Thus, FIG. 7 shows as embodiment in which the end of the rod 10 has a single taper 42 and a rounded end 43 which mate with an appropriately shaped opening in the prosthesis 5.

FIG. 8 shows an embodiment in which the end of the rod has a semi circular shape 44 with an appropriate opening in the prosthesis 5 and FIG. 9 shows the end of the rod 10 carrying a bifurcated head 45 which is shaped and dimensioned to fit over the shoulder 46 of the prosthesis 5. In this case the location feature is formed by the sides 47 and 48 of the prosthesis.

The angular position of the handle 15 in relation to the cranked extension 3 can be altered by relocating it on the square section portion 33 of the support 6. In order to rotate the handle to a different angular position the lock knob 14 is released by unscrewing it sufficiently to move the casing 11 to the right with respect to the support 6 to disengage the square section. The handle is then moved to the desired angular position and slid back onto the square section being subsequently clamped in position by the lock knob 14.

Figure 6:
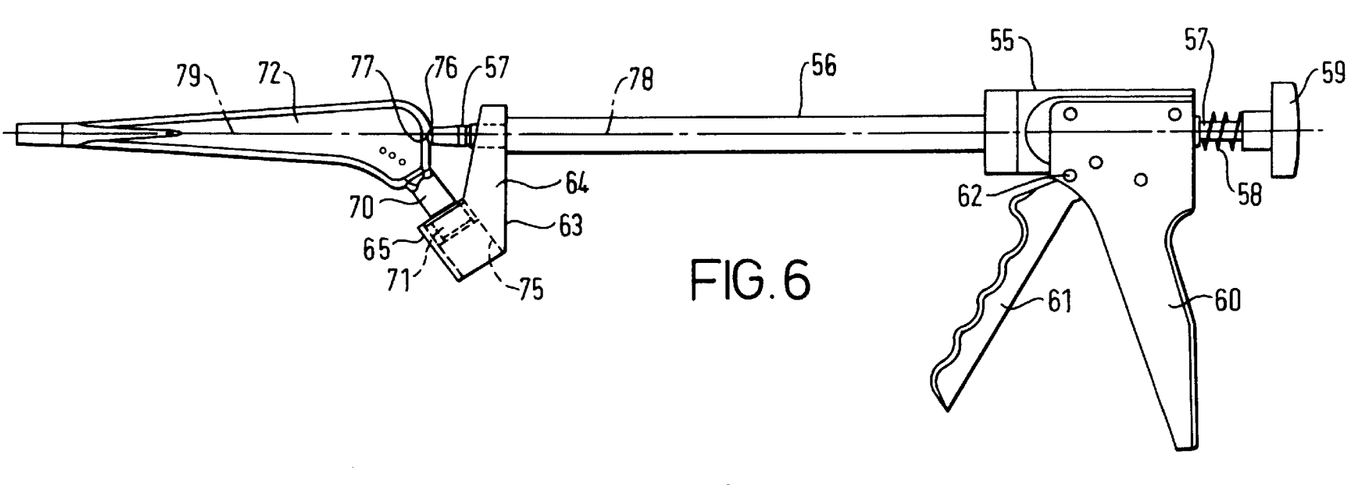
FIG. 6 is a side elevation of an alternative construction according to the invention.

FIG. 6 shows another embodiment but employing a different form of attachment device. In this arrangement a main body 55 carries a hollow extension 56 in which is mounted a retractable rod 57. The rod is biased towards a retracted position by a compression spring 58 which acts between the body 55 and an end knob 59. The body 55 carries a handle 60 and an operating trigger 61 which is pivoted to the handle by a pin 62. The end of the trigger 61 carries a bifurcated arm which surrounds a portion of reduced diameter of the rod (not shown) so that operation of the trigger acts to move the rod in a direction away from the handle and to cause the spring 58 to be compressed.

The end of the extension 56 spaced away form the handle 60 carries attachment device 63 which is provided by a bracket 64 which is rigidly attached to the extension 56. The other end of the bracket is provided with a socket 65 which is shaped to receive a spigot adapter in the form of a two piece split collet of the kind shown in FIGS. 13, 14 and 15. This collet comprises two collet portions 66 and 67 which are made from a resilient plastics material, for example polypropylene. Each of the portions 66, 67 is substantially semi circular and has a closed end provided by an upper wall 68 and a semi circular cavity 69. The cavity is shaped to correspond to the neck 70 and head 71 of the modular prothesis 72. The collet portion 67 has a flat 73 on one side and as will be seen by the drawings each of the collet portions do not extend around a full half circumference of the spigot but leave a gap 74 between them. The collet and socket 65 are dimensioned so that the collet and spigot are a press fit into the socket which is sufficient to firmly secure and hold the spigot in place, but allowing the spigot and collet to be easily withdrawn.

Figure 10:
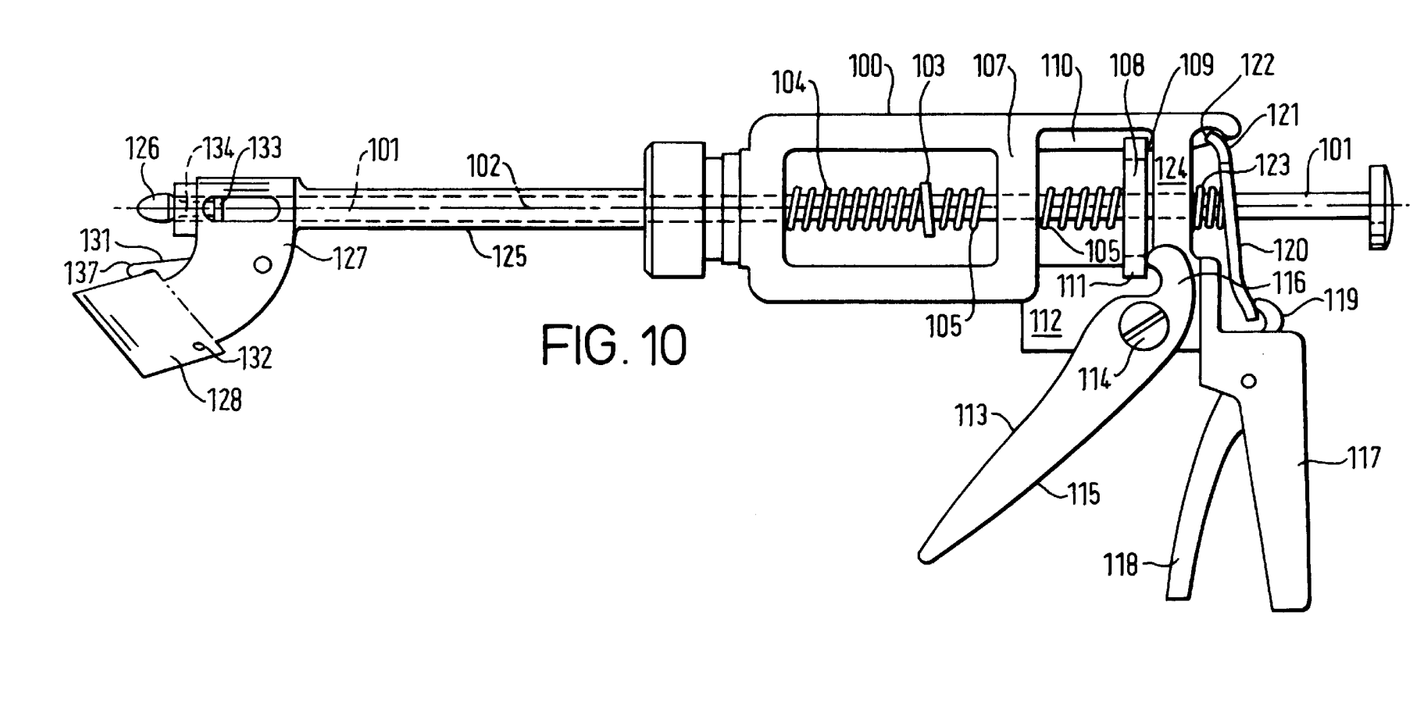
FIG. 10 is a side elevation of another embodiment according to the invention.

The socket 65 is also provided with a flat 75 on the portion of its wall intended to be adjacent the engagement wall 140 on the locking plate 131 in the construction shown in FIG. 10. The outer end of the rod 57 carries a shaped end 76 which is adapted to engage in a feature on the shoulder of the prosthesis 72 in a similar manner to the construction shown in FIG. 1 but in this construction it will be seen from FIG. 6 that the insertion axis 78 is axially aligned with the axis 79 of the prosthesis.

Figure 13:
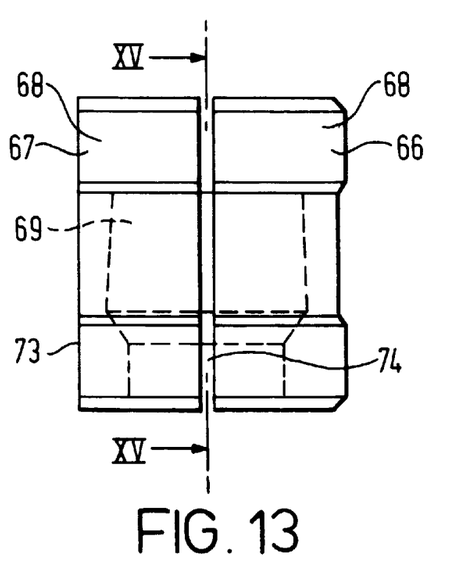
FIG. 13 is a side elevation of a two part split collet for use in the embodiment shown in FIGS. 6, 10, 11, and 12.
Figure 14:
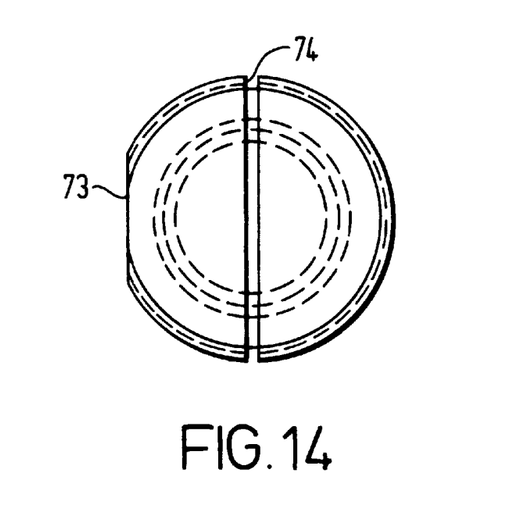
FIG. 14 is a plan view from above of the collet shown in FIG. 13.
Figure 15:
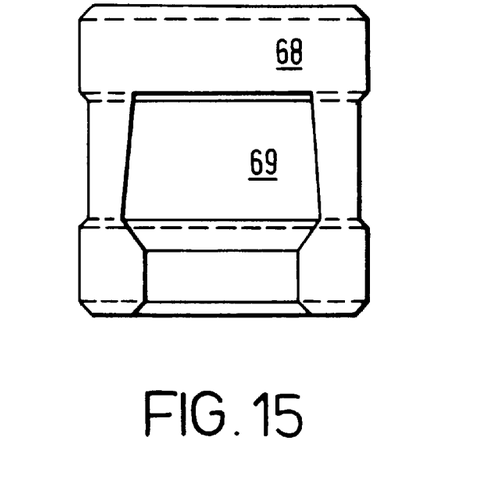
FIG. 15 is a end elevation on the lines XV—XV of FIG. 13 showing one of the collet parts.

In order to attach the inserter to the prosthesis a spigot collet of the kind shown in FIGS. 13, 14 and 15 is first located on the spigot 71 of the prosthesis and is then pushed into the socket 65. The shaped end of the rod 57 is extended against the spring 58 by operating the handle 71 so that the end 76 enters the opening in the prosthesis. The prosthesis is now firmly attached to the inserter but is prevented from rotating against axial and angular movement in relation to the insertion axis 78.

With this construction any downward insertion load by the surgeon whilst the prosthesis is implanted is partly carried by the rod 57 by the surgeon inserting a pressure on the trigger 61. Part of the load can also be carried by the attachment means 63.

When the insertion has been completed the inserter can be removed by one hand merely by relieving the pressure on the trigger 61 which allows the location means 76 and 77 to be released and the attachment means can also be released by pulling the socket 65 away from the split collet.

In the embodiment shown in FIG. 6 a locator of the kind shown in FIGS. 7, 8 and 9 can also be used.

FIG. 10 shows another embodiment according to the invention which is somewhat similar to that shown in FIG. 6 but in which a retractor is included for retaining the collet in place and a release is included for simultaneously actuating the retractable collet retainer and the retractable locator.

As shown in FIG. 10 the device comprises an open framed body 100 in which a sliding rod 101 is mounted. The axis of the rod 101 which also forms the insertion axis is indicated by reference numeral 102. The rod carries a rigidly attached collar 103 on one side of which is located a compression spring 104 the other end of which bears against the frame of the main body 100 so that the rod is biased towards the right, as shown in the drawing. Located on the other side of the collar 103 is loosely mounted short spring 105 the operation of which will be described hereafter.

A third compression spring 106 is also carried on the rod one end of which bears against a frame member 107 and the other end of which acts against an actuator 108 which is also carried on the rod and is in the form of a plate the upper end of which is provided with a slot 109 which can slide along a guide 110 in the upper part of the body frame. The lower part of the actuator 108 is cut away to provide a further guide surface 111 which can slide along a lower frame portion 112.

A first operating trigger 113 is also carried on the lower frame 112 by a pivot 114. The lower part of the first trigger 113 is formed as an operating lever 115 and the upper part 116 is shaped to engage the lower part of the actuator 108.

An extension of the lower part of the frame 112 is shaped to from a handle 117 on which is pivoted a second operating lever 118 the upper part of which is in the form of a hook 119 which engages the lower part of a locking member 120. The locking member is freely mounted on the rod 101 and the part is provided with a yoke 121 which engages on both sides of a retaining ridge 122 on the main body 100.

A fourth compression spring 123 is carried on the rod 101 between a rear frame member 124 through which the rod 101 passes and the locking member 120. The rod 101 passes from the body 100 through a tubular extension 125 and emerges as a locating pin 126 which provides locating means. A bracket 127 is carried on the end of the extension 125, and has a socket 128 which forms part of the attachment device.

Figure 11:
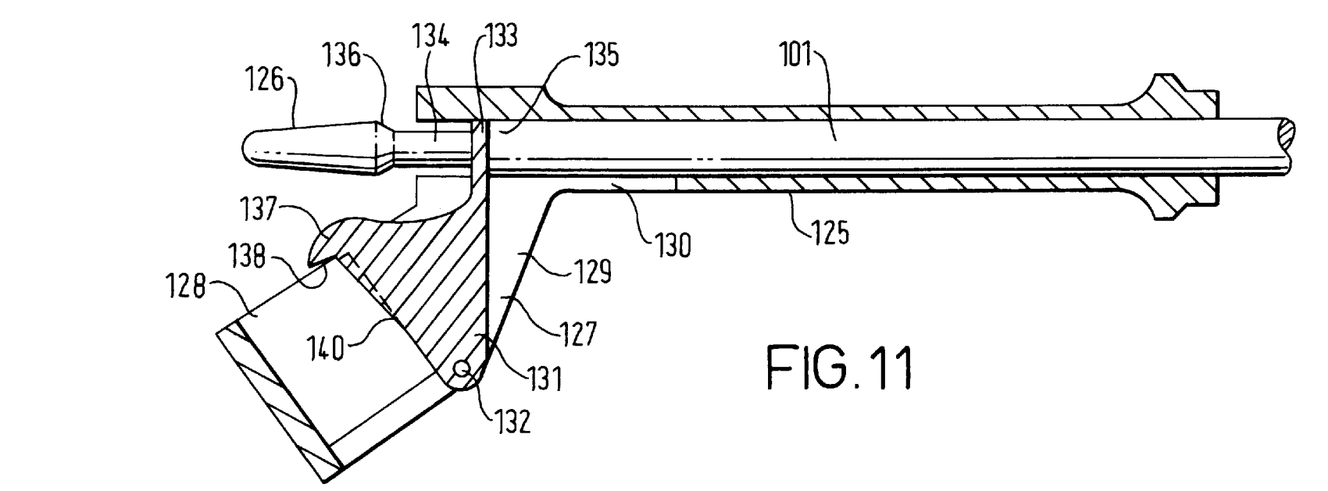
FIG. 11 is a enlarged cross-sectional side elevation of part of the embodiment shown in FIG. 10.
Figure 12:
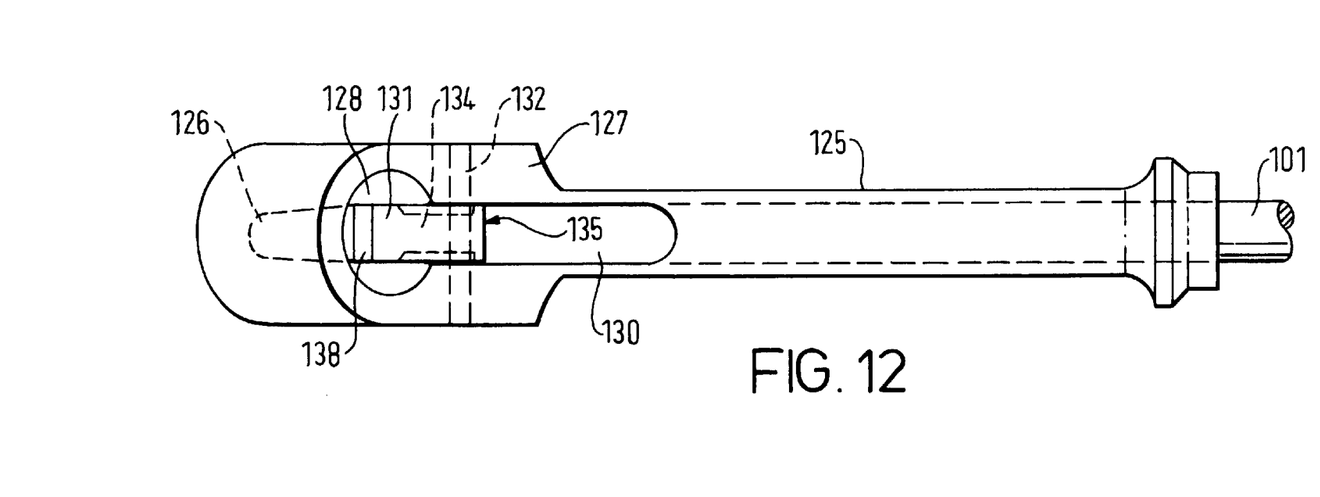
FIG. 12 is a plan view from below of the embodiment shown in FIG. 11.

The embodiment of the attachment device is most clearly shown in FIGS. 11 and 12. The side of the socket 128 is cut away to provide a slot 129 which extends through the bracket 127 and into the cylindrical extension 125 as indicated by reference numeral 130.

The collet retainer is provided in the form of a collet lock provided by a flat locking plate 131 which is located in the slot 129 and pivoted by a pin 132. The locking plate is bifurcated at 133 to provide a pair of arms which pass each side of a reduced portion 134 of the rod 101. The reduced portion 134 terminates at one end in an abutment ridge 135 and at the other in an enlargement 136 as is most clearly shown in FIG. 11. The locking plate 131 also carries a locking hook 137 having an engagement face 138 and an engagement wall 140.

The socket 128 is dimensioned to receive a split collet of the type shown in FIGS. 13, 14 and 15.

In FIGS. 10, 11 and 12 the inserter is shown in the position in which both the locating pin 126 and locking plate 131 are in the positions they take up when a prosthesis is attached to the inserter. In this position the rod 101 is in its left hand position in the body portion 100 and the first compression spring 104 is compressed. It will also be seen that the bifurcated portion 133 of the locking plate is against the abutment ridge 134 of the rod 101 which has caused the engagement face 138 of the locking hook 137 to extend over the end of the socket 128. In this position the inner face 140 extends slightly into the general curvature of the socket 128 thus acting to compress the collet when it is in position. In FIG. 11 the amount of encroachment of the face 140 has been exaggerated to show how it operates.

From FIG. 10 it will be seen that in this position the second spring 105 is still free on the rod 101 and that the third spring 106 is uncompressed and is holding the plate 108 against the trigger 113. The fourth spring 123 is still acting against the locking member 120.

The opening in the locking member 120 is slightly larger than the diameter of the operating rod 101 but because the spring 123 pushes the lever outwardly away from the frame member 124 the lever tends to rotate about the retaining ridge 122 so that the opening operates to jam against the rod 101 and prevent movement. When the second operating lever 118 is operated it rotates and the hook 119 presses against the lower end of the locking lever so that it rotates against the action of the spring 123 and thus frees the rod 101. With the rod freed from the locking member the compression spring 104 which, in the position shown in FIG. 10 is compressed, spring 104 can now operate and move against the collar 103 thus pushing the operating rod 1 to the right and into a retracted position which is determined by the enlargement 136 on the rod 101 engages the bifurcated end 133 of the locking plate this not only causes the locking plate to rotate about the pivot 132 to a retracted position where the hook 137 is clear of the socket 128 but acts to restrain the retracting movement of the rod 101.

The actuator plate 108 is a loose fit on the rod 101 so that although it can tilt under the action of the trigger 113 it then locks onto the rod 101 and acts to move it against the action of the third spring 106. Thus, the trigger can move the actuating plate to provide an "inching" movement or as a single or separate movements to advance the rod to the operating position. After each movement of the trigger, and when the trigger is relaxed, the third spring 106 pushes the actuating plate 101 to the position shown in FIG. 10 so that the plate always returns to this position after use of the trigger irrespective of the position of the rod 101.

In order to use the inserter shown in FIGS. 10, 11 and 12 the two piece collet 68 is first placed in position on the neck and tapered spigot of the prosthesis. With the rod 101 in the retracted position the collet and prosthesis are inserted into the socket 128 and the first trigger is operated to move the rod 101 into its operative position with the locating pin entering a suitable opening in the prosthesis and the hook 137 engaging over the end of the collet, at the same time the collet is slightly compressed to hold it firmly in the socket by the wall 140. The prosthesis can now be inserted by the surgeon holding the handle 117 and once the inserted had been completed the inserter can simply be removed by one hand by operating the lever 118 which releases both the locating means and the attachment means provided by the locking hook 137 and wall 140 acting on the collet. With these released the inserter can be easily removed, the whole operation being carried out by one hand.

Figure 16:
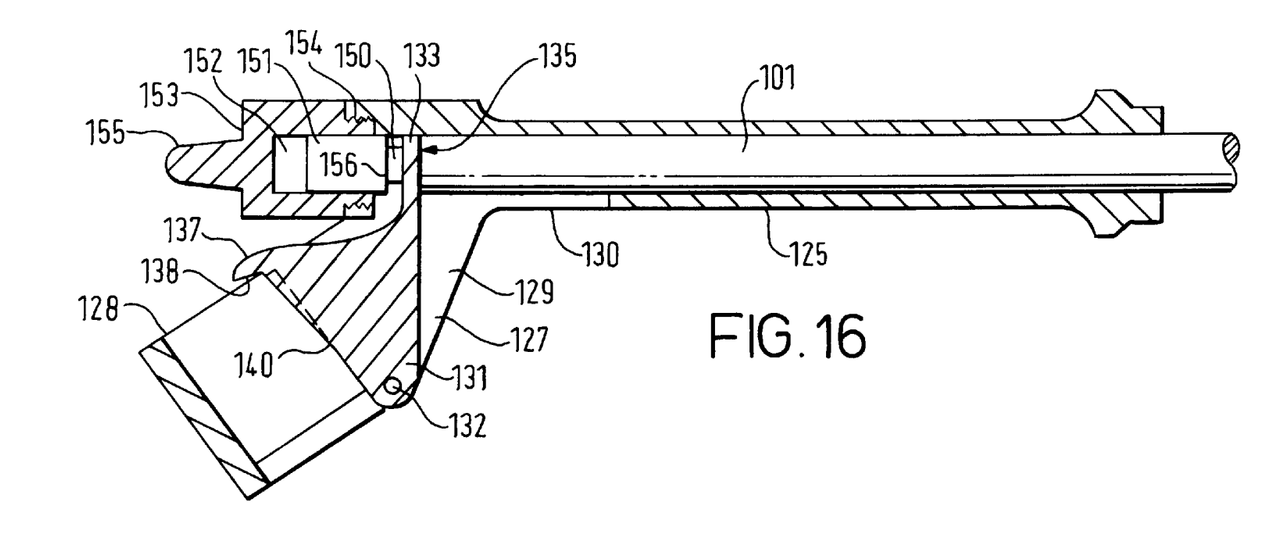
FIG. 16 is a cross-sectional side elevation of part of another embodiment according to the invention.

FIG. 16 shows yet another embodiment of to the invention which is somewhat similar to that shown in FIGS. 10 to 15 but in which the locator does not retract. The same reference numerals are used to indicate similar parts to those shown in FIGS. 10 to 12 and a split collet similar to that shown in FIGS. 13 to 15 is employed.

In this embodiment rod 101 is provided with a groove 150 and the outer end 151 of the rod is carried in a blind bore 152 provided in a housing 153. This housing is screw threaded at 154 into the outer end of the tubular extension 125. The housing is shaped to provide a locating pin 155 which is appropriately shaped to engage a suitable opening in the prosthesis. Although it will be appreciated that the shape of this locating means could be in any of the forms shown in FIGS. 7, 8 and 9.

With this embodiment the bifurcated part 133 of the locking plate which provides the pair of arms engage in the groove 150 and are acted upon by the abutment ridge 135 provided by one side of the groove. A second abutment ridge 156 provided by the other side of the groove.

The triggers 113 and 117 are operated in a similar manner to that described with regard to FIGS. 10 to 12 but it will be seen that when the rod 101 is advanced it only operates on the locking plate 131, the outer end 151 of the rod 101 sliding in the blind bore 152. Retracting of the locking plate 131 is again achieved in a similar manner to operation of the construction shown in FIGS. 10 to 12 but in this case the second abutment ridge 156 acts against the bifurcation 133 to move the locking plate 131 to its retracted position.

This embodiment is used in a similar manner to that described with regard to FIGS. 10 to 12 but in this case the location means provided by the location pin 155 is pushed into position and the trigger 113 is operated to lock the trunion into the attachment element. In order to remove the inserter the trigger 118 is operated to release the locking plate 131 so that the inserter can be removed.

Once again it will be appreciated that all the actions can be carried out with one hand and this construction demonstrates a device in which the release acts only on the locator.

It will be appreciated that although various forms of locating means can be employed, for example as shown in FIGS. 7, 8 and 9, there are others which could be equally effective. For example, a locator can be used which only engages one side wall of the prosthesis to be inserted, the device employing a flat surface which has sufficient length to effectively prevent angular rotation of the prosthesis about its spigot in both directions.

In the embodiment shown in FIGS. 18 to 22 a prosthesis inserter according to the present invention comprises a prosthesis holder which includes a tubular main body component 20 having a longitudinal axis co-axial with the insertion axis the distal end of which is attached by a fixing screw 215 which bears on a section of reduced diameter 216 to an operating handle 202. The handle 202 houses a pivotal lever 203 which rotates around pivot 214, and one end of which bears upon one end of an operating rod 204 which can travel along the insertion axis. The operating rod 203 is mounted coaxially with the main body component 201 in a bore and a spring 205 is provided between the distal end of the operating arm and the distal end of the main body component 201 to bias the rod 204 towards a rest position. The proximal end of the operating rod 204 has a shaped end 206 of reduced diameter for limited insertion into the femoral prosthesis 207. The proximal end of the main body component 201 has tapered flats 208 to produce tapering effect when inserted into a tapered socket 210 of the attachment element 209 the flats precluding torsional movement of the main body component 201 in the element 209.

Figures 18, 19, 20, 21:
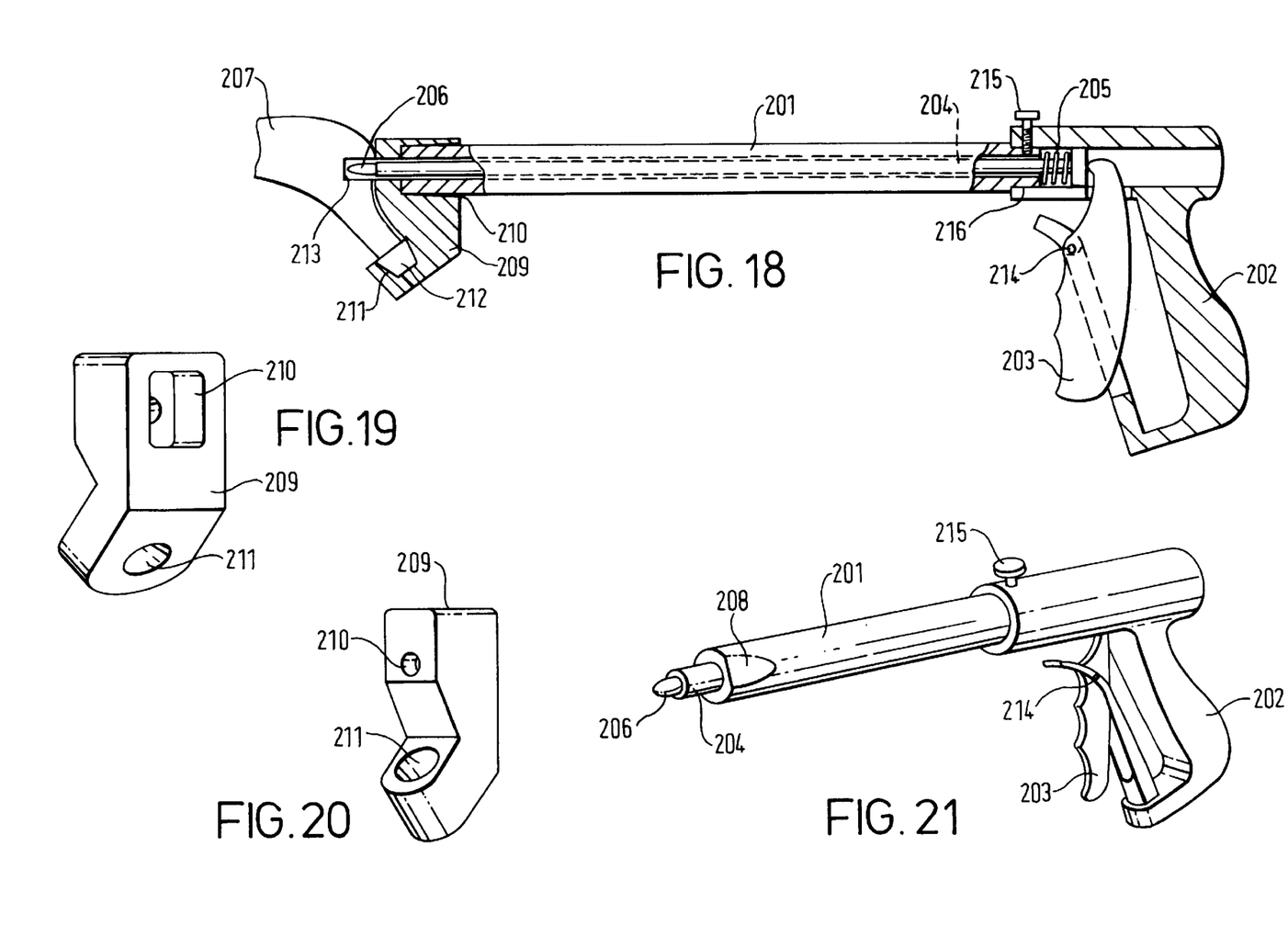
FIG. 18 is a diagrammatic part cross sectional side elevation of a first embodiment of prosthesis inserter according to the invention.
FIG. 19 is a isometric view of the attachment element shown in FIG. 18.
FIG. 20 is another isometric view of the attachment element shown in FIG. 18.
FIG. 21 is an isometric view of the prosthesis holder with the attachment element removed.

The tapered socket 210 allows limited entry of the main body component 201 while allowing full passage of the operating rod 204. The attachment element 209 also has an additional tapered socket 211 which fits over the tapered spigot 212 of the femoral prosthesis 207 to co-operate therewith and to firmly locate thereon.

An engagement feature 213 is provided on the shoulder of the prosthesis 207 for locating the shaped end of the operating rod 204 so that when engaged it ensures that the entire assembly is held rigid.

The parts are assembled by firstly firmly inserting the tapered spigot 212 of the femoral prosthesis 207 into the tapered socket 211 of the attachment element 209, then by firmly inserting the tapered end 208 of the tubular main body component into the tapered socket 210 of the attachment 209 and then the shaped end 206 of the operating rod 204 into the engagement feature 213 of the prosthesis 207.

To release the femoral prosthesis 207 the pivotal lever 203 is rotated about the pivot 214 which causes one end of the lever to bear upon the distal end of the operating rod. This causes the spring 205 to be compressed allowing the operating rod 204 to travel within the tubular main body component 201. The shaped end of 206 of the operating rod 204 is now caused to bear upon the femoral prosthesis 207 to release the tubular main body component 201 from the attachment element 209 and allowing the attachment element 209 to be released from the tapered spigot 212 of the femoral prosthesis 207.

Figures 22, 23, 24, 25:
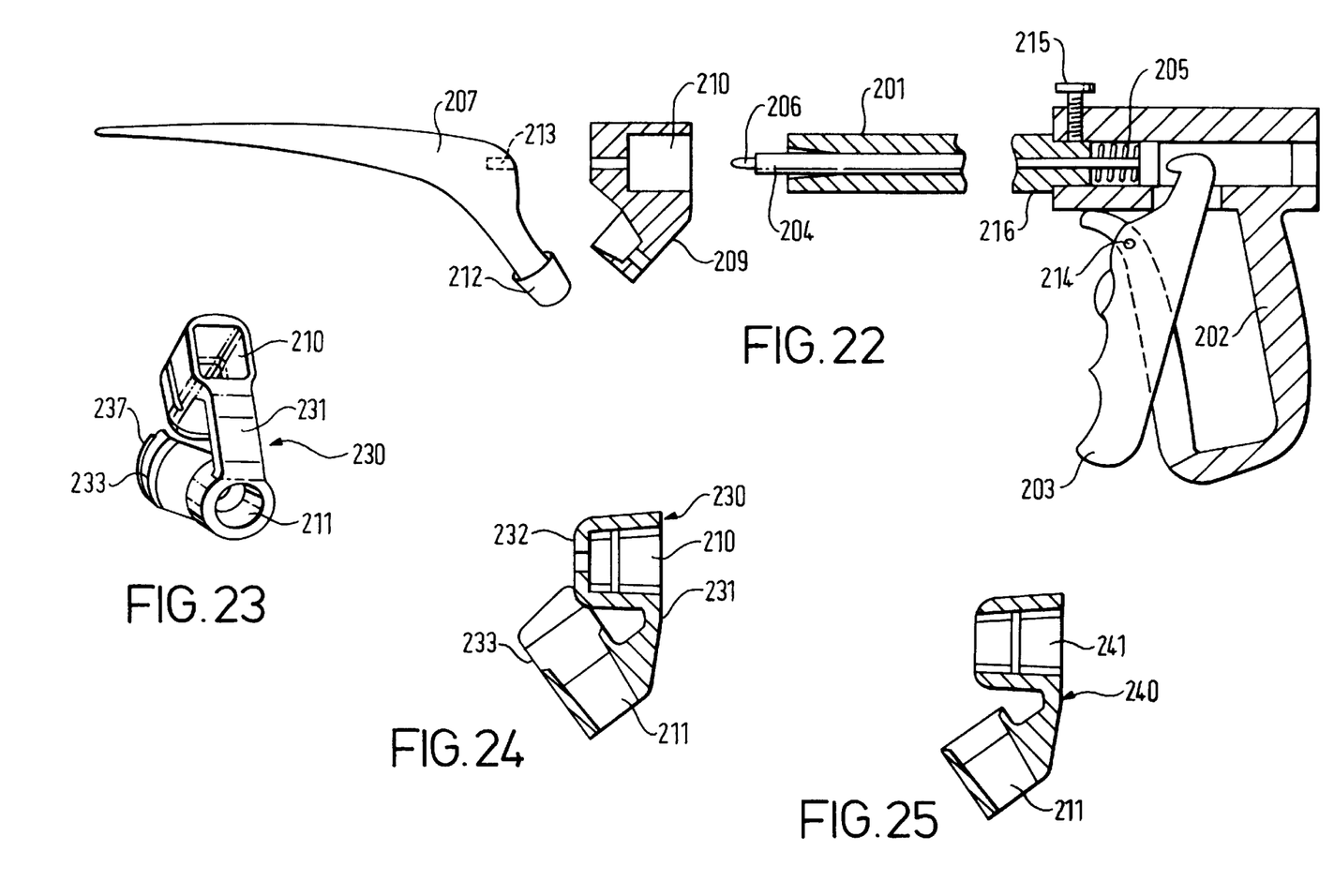
FIG. 22 is an exploded diagrammatic cross sectional side view of the prosthesis inserter according to the invention.
FIG. 23 is an isometric view of an alternative for of attachment element which can be used with the embodiment shown in FIGS. 18 to 22.
FIG. 24 is a cross-sectional side evaluation of the attachment insert shown in FIG. 23.
FIG. 25 is a cross-sectional view of another alternative construction of attachment element.

FIGS. 23 and 24 show an alternative construction of attachment element indicated by reference numeral 230. In this construction the same reference numerals are used to indicate similar parts to those shown in FIGS. 18 to 22 but in this arrangement the tapered sockets 210 and 211 are interconnected by a bridge 231 which has a slight amount of flexibility. Thus, when the parts are assembled and are in place on the prosthesis 207, the slight amount of flexibility allows the front face 232 of the portion providing the socket 210 to bear against the shoulder of the prosthesis and when the rod 204 is released to move away thus facilitating release.

The embodiment shown in FIGS. 23 and 24 is a also provided with a pair of spaced apart wings 233 to allow the connection of means to control the position and depth of the prosthesis when it is placed in position with respect to the bone into which it is to be inserted in the manner described in the Applicant's copending British Patent Application GB-A-9804471.2

FIG. 25 shows yet another embodiment of attachment element, indicated by reference numeral 240, which is similar to that shown in FIGS. 23 and 24 but in which the wings 233 are not included and the closed end of the socket 210 is deleted. Thus, the socket is replaced by a tapered bore 241 so that the end of the main body component 201 can pass through it and directly engage the shoulder of the prosthesis 212. In certain requirements there are advantages with this construction in as s much that axial forces applied by the handle through the main body component 201 can be directly transferred to the shoulder of the prosthesis. For fitting and removal the apparatus works in the same way as that described with regard to the other embodiment.

What is claimed is:

1. A prosthesis implantation inserter for inserting a prosthesis having a trunion extending therefrom into a bone comprising:

an attachment element mounted on said inserter configured for releaseable attachment to the trunion of the prosthesis for securing and holding the prosthesis to be implanted; a locator mounted on said inserter and spaced away from the attachment element and adapted to releasably engage the prosthesis to prevent axial and angular movement thereof in relation to the insertion axis of the inserter and a release mounted on the inserter engaging the locator adapted for single handed operation for releasing one or both of the attachment element and the locator from the prosthesis said attachment element includes a resilient adapter shaped to surround said trunion and an engagement having surfaces which grasp said resilient adapter said resilient adapter includes at least one claw which contacts said surfaces of said engagement element.

2. The prosthesis implantation inserter as claimed in claim 1 in which implantation loads applied to the inserter are transmitted to the prosthesis to be implanted through the attachment documents.

3. The prosthesis implantation inserter as claimed in claim 1 in which implantation loads applied to the inserter are transmitted to the prosthesis to be implanted through the locator.

4. The prosthesis implantation inserter as claimed in claim 1 wherein said prosthesis is a femoral component to be implanted, with said trunion being formed on said proximal end of said component.

5. The prosthesis implantation inserter as claimed in claim 1 in which said resilient adapter is in the form of a collet having a flange which is adapted to engage beneath the trunion.

6. The prosthesis implantation inserter as claimed in claim 5 in which said collet is split.

7. The prosthesis implantation inserter as claimed in claim 5 including an actuator element for simultaneously actuating a releasable collet retainer and said releasable locator.

8. The prosthesis implantation inserter as claimed in claim 4 in which said attachment element is adapted to attach to the trunion of said femoral component and to also receive said locator.

9. The prosthesis implantation inserter as claimed in claim 8 in which the attachment element has a tapered socket dimensioned to surround the trunion said prosthesis and a tapered socket to co-operate with a suitable portion of said inserter adjacent said locator.

10. The prosthesis implantation inserter as claimed in claim 9 in which said attachment element has a distal surface adapted to engage a proximal shoulder of the femoral component to be implanted.

11. The prosthesis implantation as claimed in claim 10 in which said attachment element is made from a synthetic material.

12. The prosthesis implantation inserter as claimed in claim 11 in which said synthetic material is polycarbonate.

13. The prosthesis implantation inserter as claimed in claim 1 in which said locator is adapted to engage a location surface on said prosthesis to be implanted.

14. The prosthesis implantation inserter as claimed in claim 13 in which said location surface is provided by a side or sides of the prosthesis.

15. The prosthesis implantation inserter as claimed in claim 14 in which the locator includes a retractable bifurcated portion slidably mounted on said inserter which includes surfaces that engage the sides of the prosthesis.

16. The prosthesis implantation inserter as claimed in claim 13 in which the locator includes a retractable pin adapted to engage a recess in the prosthesis.

17. The prosthesis implantation inserter as claimed in claim 15 in which a detent is mounted on the inserter and engagable with said slidable retractable portion to hold the retractable portion in a withdrawn position.

18. The prosthesis impantation inserter as claimed in claim 15 further including a body portion which extends along the axis of insertion, a handle, and a trigger for operating the retractable locator.

19. The prosthesis implantation inserter as claimed in claim 18 in which said trigger can act to release the attachment element and retract the locator.

20. An insertion system for a prosthesis hip implant having a stem with a locating element and a trunion formed on the proximal portion thereof comprising:

an inserter having a body;

an attachment element coupled to said body and having a bottom wall and a pair of spaced apart side walls and a crossbar extending between said side walls and spaced from said bottom wall;

a selectively retractable locator element mounted on said body for movement with respect thereto and capable of selective engagement with the locating element formed on said stem; and a resilient adapter element mountable on the trunion having a body with an internal bore shaped to resiliently receive the trunion and having an arm extending from said adapter body, said arm having a portion engaging said bottom wall of said attachment element with a portion of said arm extending between said crossbar and said bottom wall.

21. The insertion system as set forth in claim 20 wherein the body of said resilient adapter is split.

22. The insertion system as set forth in claim 20 wherein said adapter has two arms one located on each side of said split in said body.

23. The insertion system as set forth in claim 21 wherein said retractable element mounted on said inserter body is a spring loaded pin.

24. The insertion system as set forth in claim 23 wherein the locating element formed on the stem is a cavity sized to receive said pin.

25. An inserter system for inserting a prosthetic hip implant into the medullary canal of the femur, the implant having a trunion and a lateral shoulder with a depression, the trunion and shoulder located at the proximal end of the implant, the inserter system comprising:

a split adapter for mounting on the trunion having variable diameter sized to allow the adapter to be placed on the trunion when at a first diametric size and to tightly capture said trunion when at a second smaller diametric size;

a handle having a retractable rod mounted thereon selectively moveable into and out of engagement with said depression on the shoulder of the implant;

a spring loaded actuator mounted on the said handle for controlling said selective movement of said rod into and out of engagement with said depression; and an engagement element mounted on said handle for engaging an outer surface of said adapter and moving the diameter thereof from said first to said second size.

\* \* \* \* \*

UNITED STATES PATENT AND TRADEMARK OFFICE
CERTIFICATE OF CORRECTION

PATENT NO. : 6,113,605
DATED : September 5, 2000
INVENTOR(S) : Storer

Page 1 of 3

It is certified that error appears in the above-identified patent and that said Letters Patent is hereby corrected as shown below:

On the face of the patent:
  Under Attorney, Agent or Firm, line 2, "Mentlink" should read -- Mentlik --.

Column 1, line 46, "releases" should read -- released --.
Column 1, line 54, after "comprises", insert -- an --.
Column 2, line 18, "prothesis" should read -- prosthesis --.
Column 2, line 26, after "have", insert -- a --.
Column 2, line 51, "single handed" should read -- single-handed --.
Column 2, line 53, after "desired", insert -- structure --.
Column 2, line 63, "location" should read -- located --.
Column 3, line 3, "a" should read -- an --.
Column 3, line 9, "a" should read -- an --.
Column 3, line 18, "a" should read -- an --.
Column 3, line 26, "cross sectional" should read -- cross-sectional --.
Column 3, line 29, "a" should read -- an --.
Column 3, line 35, "cross sectional" should read -- cross-sectional --.
Column 3, line 37, "for" should read -- form --.
Column 3, line 48, cancel "a prosthesis".
Column 4, line 31, "mostly" should read -- most --.
Column 4, line 44, "is" should read -- are --.
Column 5, line 5, "engage" should read -- engages --.
Column 5, line 6, "prevent" should read -- prevents --.
Column 5, line 21, "are" should read -- is --.

UNITED STATES PATENT AND TRADEMARK OFFICE
CERTIFICATE OF CORRECTION

PATENT NO.    : 6,113,605
DATED         : September 5, 2000
INVENTOR(S)   : Storer It is certified that error appears in the above-identified patent and that said Letters Patent is hereby corrected as shown below:

Column 5, line 26, "embodiment" should read -- embodiments --.
Column 5, line 27, "as" should read -- an --.
Column 7, line 13, after "124", insert -- , --.
Column 7, line 14, after "passes" (first occurrence), insert -- , --.
Column 8, line 1, after "10", insert -- , --.
Column 8, line 4, after "101", insert -- which --.
Column 8, line 5, after "plate", insert -- , --.
Column 8, line 13, "movements" should read -- movement --.
Column 8, line 36, cancel "to".
Column 8, line 56, after "156", insert -- is --.
Column 9, line 33, after "produce", insert -- a --.
Column 9, line 35, after "209", insert -- , --.
Column 9, line 60, cancel "of" (first occurrence).
Column 10, line 10, cancel "a".
Column 10, line 11, "spaced apart" should read -- spaced-apart --.
Column 10, line 25, cancel "s".
Column 10, line 42, "single handed" should read -- single-handed --.
Column 10, line 53, "documents" should read -- element --.
Column 12, line 2, "spaced apart" should read -- spaced-apart --.
Column 12, line 20, after "arms", insert -- , --.

UNITED STATES PATENT AND TRADEMARK OFFICE
CERTIFICATE OF CORRECTION

PATENT NO. : 6,113,605  
DATED : September 5, 2000  
INVENTOR(S) : Storer

Page 3 of 3

It is certified that error appears in the above-identified patent and that said Letters Patent is hereby corrected as shown below:

Column 12, line 24, "spring loaded" should read -- spring-loaded --.  
Column 12, line 42, "spring loaded" should read -- spring-loaded --.

Signed and Sealed this

First Day of May, 2001

Attest:

NICHOLAS P. GODICI

Attesting Officer     Acting Director of the United States Patent and Trademark Office